(12) United States Patent
Müeller et al.

(10) Patent No.: US 7,223,261 B2
(45) Date of Patent: May 29, 2007

(54) ARTICLES WITH ELASTICATED TOPSHEETS

(75) Inventors: Joerg Müeller, Karben (DE); Lars Westerheide, Kelkheim (DE); Mattias Schmidt, Idstein (DE); Frederick Michael Langdon, Blue Ash, OH (US); Michael Divo, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 229 days.

(21) Appl. No.: 10/764,850

(22) Filed: Jan. 26, 2004

(65) Prior Publication Data
US 2004/0162538 A1    Aug. 19, 2004

Related U.S. Application Data

(63) Continuation of application No. PCT/US02/23643, filed on Jul. 25, 2002.

(51) Int. Cl.
*A61F 13/15*    (2006.01)
(52) U.S. Cl. ............ 604/385.19; 604/385.01; 604/385.24
(58) Field of Classification Search ........ 604/385.01, 604/385.19, 385.22, 385.24, 385.09, 385.28, 604/348
See application file for complete search history.

(56) References Cited

U.S. PATENT DOCUMENTS

| 3,848,594 A | 11/1974 | Buell |
| 3,860,003 A | 1/1975 | Buell |
| 3,929,135 A | 12/1975 | Thompson |
| 4,324,246 A | 4/1982 | Mullane et al. |
| 4,342,314 A | 8/1982 | Radel et al. |
| 4,463,045 A | 7/1984 | Ahr et al. |
| 4,515,595 A | 5/1985 | Kievit et al. |
| 4,609,518 A | 9/1986 | Curro et al. |
| 4,610,678 A | 9/1986 | Weisman et al. |
| 4,629,643 A | 12/1986 | Curro et al. |
| 4,662,875 A | 5/1987 | Hirotsu et al. |

(Continued)

FOREIGN PATENT DOCUMENTS

EP        0 433 951 A2    6/1991

(Continued)

OTHER PUBLICATIONS

Search report for WO 03/009795 A1 published Feb. 2003, Schmidt et al., WIPO.*

Primary Examiner—Tatyana Zalukaeva
Assistant Examiner—Michael G Bogart
(74) Attorney, Agent, or Firm—Michael P. Hayden; Eric T. Addington; Thibault Fayette

(57) ABSTRACT

The invention relates to an absorbent, disposable article, preferably a diaper, having a backsheet and a topsheet comprising a first waist region, a second waist region, and a crotch region interposed there between, a longitudinal axis, and an opening, which provides a passageway to a primary void space for receiving bodily exudates therein, positioned between the topsheet and the backsheet; whereby the opening is positioned in at least the crotch region along the longitudinal axis; whereby the topsheet is elasticated; and whereby the article has a shortened article portion, as defined herein, which has a shortened article length L, a stretched shortened article length $L_s$ and a contacted shortened article length $L_c$, whereby the article and/or its topsheet has an specific elastic profile and/or a specific ratio of $L_c$ to $L_s$.

6 Claims, 3 Drawing Sheets

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,116 A * | 11/1987 | Enloe | 604/385.27 |
| 4,795,454 A | 1/1989 | Dragoo | |
| 4,808,178 A | 2/1989 | Aziz et al. | |
| 4,834,735 A | 5/1989 | Alemany et al. | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 4,988,344 A | 1/1991 | Reising | |
| 4,988,345 A | 1/1991 | Reising | |
| 4,990,147 A | 2/1991 | Freeland | |
| 5,137,537 A | 8/1992 | Herron et al. | |
| 5,147,345 A | 9/1992 | Young et al. | |
| 5,151,092 A | 9/1992 | Buell et al. | |
| 5,156,911 A | 10/1992 | Stewart | |
| 5,221,274 A | 6/1993 | Buell et al. | |
| 5,260,345 A | 11/1993 | DesMarais et al. | |
| 5,387,207 A | 2/1995 | Dyer et al. | |
| 5,387,450 A | 2/1995 | Stewart | |
| 5,439,459 A * | 8/1995 | Tanji et al. | 604/385.28 |
| 5,518,801 A | 5/1996 | Chappell et al. | |
| 5,607,760 A | 3/1997 | Roe | |
| 5,609,587 A | 3/1997 | Roe | |
| 5,625,222 A | 4/1997 | Yoneda et al. | |
| 5,635,191 A | 6/1997 | Roe et al. | |
| H1670 H | 7/1997 | Aziz | |
| 5,643,588 A | 7/1997 | Roe et al. | |
| 5,648,167 A | 7/1997 | Peck | |
| 6,648,869 B1 * | 11/2003 | Gillies et al. | 604/385.28 |
| 2001/0004689 A1 * | 6/2001 | Otsubo | 604/385.19 |
| 2006/0025744 A1 * | 2/2006 | Mishima et al. | 604/385.101 |

FOREIGN PATENT DOCUMENTS

| | | |
|---|---|---|
| EP | 1 106 152 A | 6/2001 |
| GB | 2 287 888 A | 4/1995 |
| GB | 2284550 | 6/1995 |
| GB | 2 297 473 A | 7/1996 |
| GB | 2 328 158 A | 2/1999 |
| GB | 2 329 842 A | 4/1999 |
| WO | WO 95 24173 A2 | 9/1995 |
| WO | WO 98 08476 A | 3/1998 |

* cited by examiner

ARTICLES WITH ELASTICATED TOPSHEETS

This application is a continuation of PCT/US02/23643 filed Jul. 25, 2002.

FIELD OF THE INVENTION

This invention is directed to absorbent articles, such as diapers, training pants, adult incontinence articles, feminine protection articles and the like having a specific elasticated topsheet.

BACKGROUND OF THE INVENTION

Wearable absorbent articles are well known in the art. These articles typically have an absorbent core, which is held or positioned against the body of the wearer during use by a fastening system, such that the bodily exudates are caught by the article. Typical absorbent articles include a topsheet facing the wearer, which permits fluid exudates to pass through, and a backsheet which prevents the exudates from escaping from the absorbent article.

Much advancement has been made in the art since the introduction of the disposable absorbent article. However, problems still exist relating to the acceptance and storage of feces. The problem has been difficult to resolve because feces generally will not pass through a topsheet and thus, remains free to move about in the diaper until the diaper is changed. This often leads to feces escaping the diaper or soiling of the wearer's skin. In particular fluid feces has this problem, since it is very mobile on the topsheet and easily moves from one side to another and easy escapes the diaper's leg portions or leg cuffs.

In order to prevent the feces from escaping the absorbent article or soiling the skin, apertures have been provided in the top sheet, which allow the feces to pass to a void space disposed between the topsheet and underlying layers of the diaper. However, the apertures are difficult to position during application of the article and often move from the desired position when the article is worn.

Some degree of success has been achieved using an elastically foreshortened topsheet having a generally elliptical aperture to allow feces passage and retention away from the skin. These articles are disclosed in U.S. Pat. No. 4,892,536 issued to DesMarais and U.S. Pat. No. 4,990,147 issued to Freeland. These approaches have the limitation of not maintaining alignment of the opening with the wearer's anus in one or more of the longitudinal, lateral or z-direction axes of the article. Further, if the opening shifts laterally to a significant degree, the opening may achieve a geometric lock on the edge of the buttocks, decreasing the likelihood of proper aperture alignment with the anus.

Thus, it would be desirable to provide an improved absorbent article having an opening providing a passageway to a void space for receiving bodily exudates with improved fit and alignment capability which can be sustained during use, and which is such that the bodily fluids are more completely and effectively collected in said void space, or even such that about all solid fecal matter is collected in said void space.

The inventors have now found a way to solve this problem, by providing a topsheet containing elasticated regions which have a specific force profile and/or topsheets which have a specific elastic profile, and/or articles which have such a specific force profile through which they have a certain stretched and contracted length. The articles of the invention are such that the correct alignment is achieved when the article is first applied, independent on whether the article is applied correctly, and such that the correct alignment is remained in use. The article of the invention remain the correct alignment even when the wearer moves around, and even when the article is pulled down by the waist of the collected bodily fluids. The article has such an elastic profile that the slit opening remains located around the anus of the wearer, but also against the skin of the wearer, to reduce the risk that feces can escape to void space under the slit opening and to avoid the risk that the feces still moves freely on the topsheet and even leaks from the article.

SUMMARY OF THE INVENTION

The invention provides in a first embodiment an absorbent article, such as a disposable absorbent article like a diaper, training pants, adult incontinence article, feminine protection article, having a backsheet and a topsheet comprising a first waist region, a second waist region, and a crotch region interposed there between, a longitudinal axis, and an opening, which provides a passageway to a primary void space for receiving bodily exudates therein, positioned between the topsheet and the backsheet; whereby the opening is positioned in at least the crotch region along the longitudinal axis; whereby the topsheet is elasticated; and whereby the article has a shortened article portion, as defined herein, which has a shortened article length L, a stretched shortened article length $L_s$, the article having a topsheet with a shortened topsheet length Lt, and an elastic profile of:

1.5Lt by a first load force of less than 1.1N, 3.0Lt by a first load force of less than 2.1N and 4.5Lt by a first load force of less than 3.0N and a second unload force at 4.5Lt of more than 0.9N, a second unload force at 3.0Lt of more than 0.5N and a second unload force at 1.5Lt of more than 0.1N.

In another embodiment of the invention, the article has a backsheet and a topsheet comprising a first waist region, a second waist region, and a crotch region interposed there between, a longitudinal axis, and an opening, which provides a passageway to a primary void space for receiving bodily exudates therein, positioned between the topsheet and the backsheet; whereby the opening is positioned in at least the crotch region along the longitudinal axis; whereby the topsheet is elasticated; and whereby the article has a shortened article portion, as defined herein, which has a shortened article length L, a stretched shortened article length $L_s$ and the article it self has a specific elastic profile, and preferably a topsheet with a elastic profile as above, of:

$0.25L_s$ by a first load force of less than 0.6 N, $0.55L_s$ by a first load force of less than 5N or even less than 3.5 N and $0.8L_s$ by a first load force of less than 10.0N or even less than 7.0N and a second unload force at $0.55L_s$ of more than 0.4N, and a second unload force at $0.80L_s$ of more than 1.4N or even more than 2.0N.

The invention also relates to an absorbent article, having a backsheet and a topsheet comprising a first waist region, a second waist region, and a crotch region interposed there between, a longitudinal axis, and an opening, which provides a passageway to a primary void space for receiving bodily exudates therein, positioned between the topsheet and the backsheet; whereby the opening is positioned in at least the crotch region along the longitudinal axis; whereby the topsheet is elasticated and whereby the article has a shortened article portion, as defined herein, with a shortened article length L, a stretched shortened article length $L_s$ and a contracted shortened article length $L_c$, whereby the article has such an elastic profile $L_c$ is less than $0.5L_s$, preferably less than $0.35L_s$.

The invention also relates to absorbent articles having a combination of the topsheet elastic profile and/or the article elastic profile and the relationship of $L_s$ and $L_c$, as described above and hereinafter.

The invention also relates to preferred articles, preferably diapers and training pants, having the features above and a specific slit opening leading to the void space, having on the slit opening edges elastic regions, of specific shapes, orientations and elastic profiles.

DETAILED DESCRIPTION OF THE INVENTION

Figure 1:
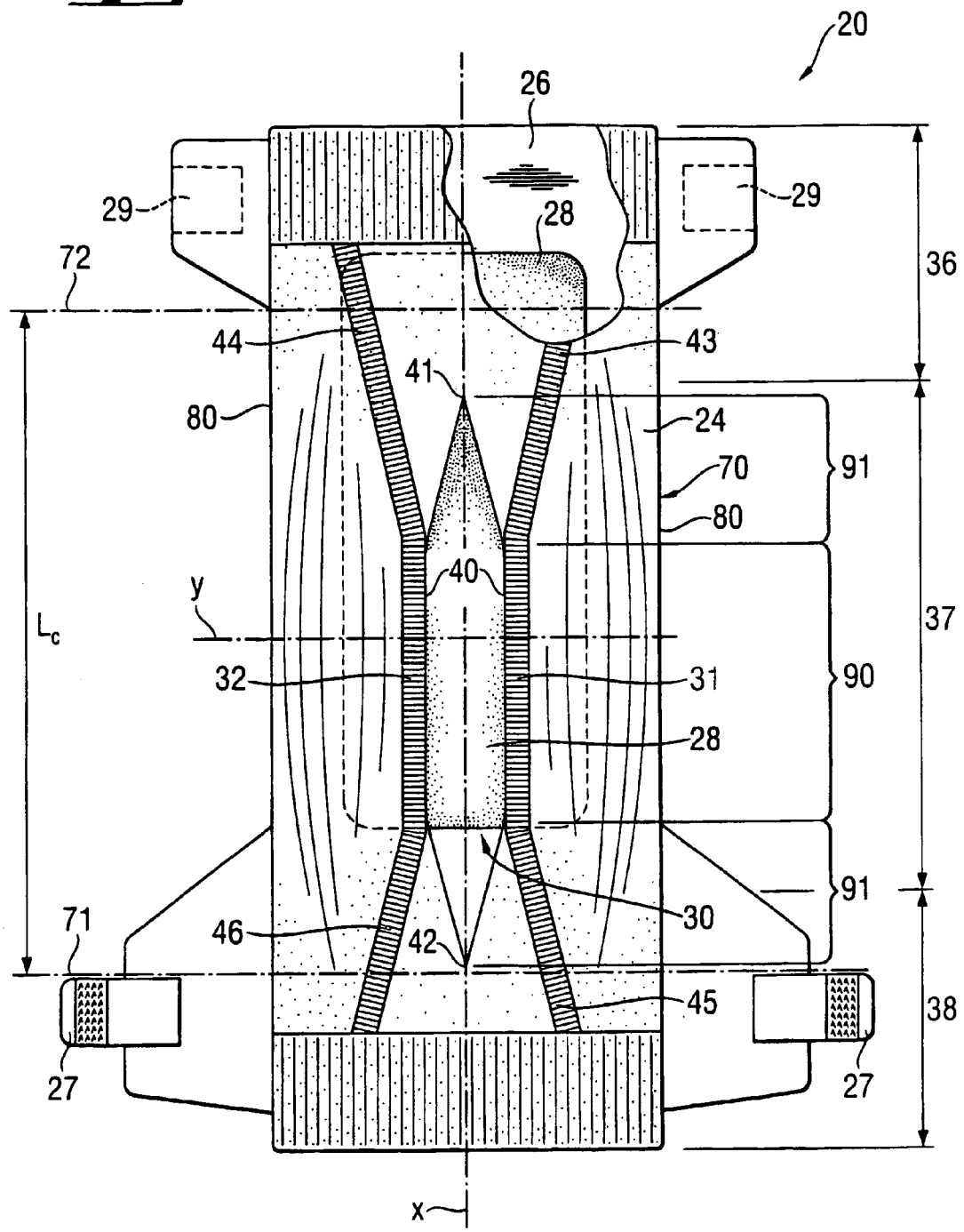
FIG. 1 is a plan view of a preferred disposable diaper configuration of the present invention.

The present invention provides a wearable absorbent article having a topsheet with an opening therein, typically an elongate split opening, which is in communication with a void space, which is suitable to receive or even store bodily exudates. In one embodiment of the invention, the article has a shortened article portion with a length L, a stretched shortened article length $L_s$ and a contracted shortened article length $L_c$, and preferably a specific unload force, load force and/or two-cycle hysteresis or elastic force profile.

As used herein, the following terms have the following meanings:

"Absorbent article" refers to wearable devices, which absorb and/or contain liquid, and more specifically, refers to devices, which are placed against or in proximity to the body of the wearer to absorb and contain the various exudates discharged from the body.

"Longitudinal" is a direction running parallel to the maximum linear dimension, typically the longitudinal axis, of the article and includes directions within 45° of the longitudinal direction.

"Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, e.g., in the same plan of the majority of the article and the longitudinal axis, and the transverse direction is parallel to the transverse axis.

"Width" of the article or of a component thereof, when used herein, refers to the size/distance of the dimension orthogonal to the longitudinal direction of the article or component thereof, e.g., orthogonal to the length of the article or component thereof, and typically it refers to the distance/size of the dimension parallel of the transverse axis of the article or component.

The "Z-direction" is orthogonal to both the longitudinal and transverse directions, e.g., running parallel to the minimum linear dimension of the article.

"Thickness" of the article or component thereof, when used herein, refers to the size/distance of the z-direction dimension.

As used herein, the term "attached" encompasses configurations whereby an element is directly secured to another element by affixing the element directly to the other element.

As used herein, the term "joined" or "connected" encompasses configurations whereby an element is directly secured to another element by affixing the element directly to the other element, and configurations whereby an element is indirectly secured to another element by affixing the element to intermediate member(s) that in turn are affixed to the other element.

As used herein, the term "diaper" refers to an absorbent article generally worn by infants and incontinent persons about the lower torso.

As used herein, the term "void space" is a cavity sized to accept and contain bodily exudates such as fecal material, present in at least the relaxed sate of the article.

As used herein "relaxed" or "relaxed state" means the state that no forces are applied to the article (other than naturally occurring forces such as gravity); this typically includes the state of the article herein, whereby L equals $L_c$, as defined below.

As used herein, "stretched" or "stretched state" means that the article is stretched to the point that the shortened article portion has the length $L_s$.

As used herein, "elasticated" and "elasticated topsheet" means, that the item or the topsheet comprises at least a portion made of elastic material, which is elastic in at least the longitudinal direction, including the situation that the topsheet as a whole is of elastic materials (elastically extendible in longitudinal direction) and/or that the topsheet contains elastic bands or strands, elastically extendible in longitudinal direction.

As used herein, "along the longitudinal axis" means at least partially parallel to the longitudinal axis.

In one embodiment, the absorbent article of the invention has a shortened article portion with a shortened article length L, a stretched shortened article length $L_s$ and a contracted shortened article length $L_c$.

The shortened article portion is the portion of the article where the existence of the specific force profiles as defined herein are particularly beneficial, typically the portion of the article between the force lines in use, e.g., if the article is a diaper, worn by a (fastened) waistband around the waist of the wearer, who is in upright position, then the front force line is typically the horizontal line where the front waist band starts (i.e., the lowest point) and the back force line is the horizontal line where the back waist band starts (i.e., the lowest point), and the shortened article portion is the portion of the diaper between these two force lines. Because it is often difficult to determine the exact location of the force lines, the shortened article portion is for the purpose of the invention defined as follows.

If an article has a front waist region or waistband and a back waist region or waistband, whereby each of the back and front waist regions has a first longitudinal edge and a second longitudinal edge, and if each longitudinal edge has a fastening means, capable of fastening the front waist region to the back waist region, whereby each fastening means on the front waist region has a lowest point (which is the point closest to the transverse axis of the article), then the shortened article portion is the portion between the transverse line between the lowest point of the fastening means of the front waist band and the transverse line between the lowest points of the fastening means of the back waist region.

(The shortened article length L is then thus the length of the longitudinal axis of this shortened article portion.)

If an article has no such fastening means but a front waist region or waistband and a back waist region or waist band which are prior to use, (irremovably) connected by a first connection area and a second connection area, positioned above the side of the leg of the wearer (such as is the case with so-called infant training pants, whereby the opposing sides are welded or seamed together), then the shortened article portion is determined by opening the connecting areas of article in the direction parallel to the longitudinal axis of the article, to obtain an article which has a front waist region with an opened connection area on each longitudinal edge and a back waist region, which has an opened connection area on each longitudinal edge, whereby each connection area on the front waist region has a lowest point (which is the point closest to the transverse axis of the article), then, the shortened article portion is the portion between the transverse line between the lowest point of the front waist region and the transverse line between the lowest points of the back waist region. The shortened article length is then the length of the longitudinal axis of the shortened article portion.

In the third case, for other articles than those above, the shortened article portion is determined by removing from each transverse end of the article a transverse strip with a width (e.g., the dimension parallel to the longitudinal axis of the article) of 20% of the articles total length (in relaxed state), so that the shortened article portion is the middle 60% of the article (in relaxed state). The shortened article length is then the length of the longitudinal axis of the shortened article, e.g., about 60% of the article length.

The latter, third method for determining the shortened article portion may also be used to determine the shortened article portion of the articles above in the first two cases, having fastening means or connecting areas, provided that the resulting article portion measured with this third test, has a smaller length than when measured with the first or second method set out above. Thus in a preferred embodiment herein the shortened article portion of each article of the invention is the middle 60% of the article, thus, the article whereof on each transverse end a transverse strip of 20% of the length of the article is removed. Then, the shortened article length is thus typically 60% of the article length.

Even more preferred may be that the shortened article portion is the middle 40% of the article, thus, the article whereof on each transverse end a transverse strip of 30% of the length of the article is removed, and the shortened article length for an article herein is then typically 40% of the length of the article.

The stretched shortened article length $L_s$ is determined as follows:

The article is placed between to clamps in a horizontal tensile tester Z10/LH 1S, as available from Zwick (Ulm, Germany). The clamps have at least the same size as the width of the article, so that the clamps at least cover the total width of the article.

The clamps are positioned such that exactly the shortened product portion is between the clamps and such that exactly (and only) the shortened product length is not covered by the clamps. The initial clamp distance should then be 4 cm. The measurement is done in a controlled environment, whereby the temperature is kept constant at 23° C. and the humidity on 50%. The article is then pulled in horizontal, longitudinal direction up to the moment that a force of 20N is applied. Then, the distance between the clamps and thus between the transverse ends of the shortened article portion is measured. This is the stretched shortened article length $L_s$.

The contracted shortened article length $L_c$ is determined as follows:

After the measurement of $L_s$ above is done, the article is rested for an hour, in the controlled conditions set out above. Then, whilst still under the controlled conditions, the article is placed in the top clamp of a vertical tensile tester (as available from Zwick). On the other end a clamp with a weight of 10 grams is placed, but still supported so that the weight does not start pulling yet due to gravity.

The clamps are positioned such that exactly the shortened product length is not covered by the clamps and thus that the end of the clamps are positioned exactly at the ends of the shortened article portion. The clamps have at least the size of the width of the article at the clamping point, so that the clamps cover the total width of the article.

Then, the support for the weight is removed and the weight is hung down for 5 minutes. Then, the distance between the clamps and thus the distance between the ends of the shortened article portion is measured. This is the contracted shortened article length $L_c$.

In one embodiment of the invention, the article has an $L_c$ which is less than $0.5L_s$ of the article. Preferably, $L_c$ of the article is less than $0.45L_s$ of the article, or even less than $0.4L_s$, or even less than $0.35L_s$, or even less than $0.3L_s$.

In another embodiment of the invention, the article has a topsheet, which has a specific elastic profile, in order to provide the benefits of the invention, and thereto, it typically comprises one or more of the elasticated regions specified herein, having an about similar elastic profile. The topsheet than has a shortened topsheet portion with a length Lt and a contracted or relaxed shortened topsheet length $Lt_c$ and a stretched shortened topsheet length $Lt_s$, determined in the manner set out above for the article.

The topsheet of the article has an elastic profile, based on a two-cycle hysteresis, measured by the method below, using a 500 mm/min clamp speed, which is as follows:

1.5Lt by a first load force of less than 1.1N, 3.0Lt by a first load force of less than 2.1N and 4.5Lt by a first load force of less than 3.0N and a second unload force at 4.5Lt of more than 0.9N, a second unload force at 3.0Lt of more than 0.5 and a second unload force at 1.5Lt of more than 0.1N.

More preferably, the profile of the topsheet is:

1.5Lt by a first load force of less than 0.6 N, 3.0Lt by a first load force of less than 1.1N and 4.5Lt by a first load force of less than 1.5N and a second unload force at 4.5Lt of more than 0.9N, a second unload force at 3.0Lt of more than 0.5N and a second unload force at 1.5Lt of more than 0.1N.

Preferred profiles of the topsheet are defined by the first load force and second load forces at all of the lengths in the following table (for a two cycle hysteresis with 500 mm/min clamp speed, stretching as set out below, up to 4.5Lt or $0.8L_s$, which ever is smaller):

|  | Preferred profile | More preferred profile | Most preferred profile |
| --- | --- | --- | --- |
| 1st load force at 1.5 Lt | <1.1 N | <1.1 N | <0.6 N |
| 1st load force at 2.0 Lt | <1.5 N | <1.5 N | <0.8 N |
| 1st load force at 2.5 Lt* | <1.8 N | <1.8 N | <0.9 N |

-continued

|  | Preferred profile | More preferred profile | Most preferred profile |
|---|---|---|---|
| 1st load force at 3.0 Lt* | <2.1 N | <2.1 N | <1.1 N |
| 1st load force at 3.5 Lt* | <2.3 N | <2.3 N | <1.2 N |
| 1st load force at 4.0 Lt* | <2.6 N | <2.6 N | <1.3 N |
| 1st load force at 4.5 Lt* | <3.0 N | <3.0 N | <1.5 N |
| 2nd unload force at 1.5 Lt | >0.1 N | >0.2 N | >0.1 N |
| 2nd unload force at 2. Lt | >0.3 N | >0.6 N | >0.3 N |
| 2nd unload force at 2.5 Lt* | >0.4 N | >0.8 N | >0.4 N |
| 2nd unload force at 3.0 Lt* | >0.5 N | >1.0 N | >0.5 N |
| 2nd unload force at 3.5 Lt* | >0.6 N | >1.2 N | >0.6 N |
| 2nd unload force at 4.0 Lt* | >0.7 N | >1.4 N | >0.7 N |
| 2nd unload force at 4.5 Lt* | >0.9 N | >1.8 N | >0.9 N |

*These values are only relevant as long as they are below 0.8 $Lt_s$, as mentioned below in the test method.

The above elastic profile of the shortened topsheet is measured by the following method, measuring the two-cycle hysteresis of said shortened topsheet portion (following ASTM 76–96):

The topsheet of an article is placed between to clamps in a horizontal tensile tester Z10/LH 1S, as available from Zwick (Ulm, Germany). The clamps are positioned such that exactly the shortened topsheet portion is between the clamps and such that exactly and only the shortened topsheet length is not covered by the clamps (i.e. the shortened topsheet portion being that part of the topsheet that belongs to the shortened article (portion), as set out above). The clamps have at least the same size as the width of the topsheet in the clamps, so that the clamps at least cover the total width of the topsheet in the clamps. The initial clamp distance should then be 4 cm. The measurement is done in a controlled environment, whereby the temperature is kept constant on 23° C. (+/−2° C.) and the humidity on 50% (+/−2%).

The two-cycle hysteresis test is then performed, stretching the shortened topsheet (portion) up to 4.5Lt, or 0.8$Lt_s$, which ever is the smallest value, while measuring the forces applied on the shortened topsheet during the stretching at the various stretching stages/lengths; when 4.5Lt or 0.8$Lt_s$ is reached, the shortened topsheet is kept in that position for 60 seconds, before the controlled relaxation back to the original position of the clamps, i.e., 4 cm distance (and the unload forces may be measured at the various stages/lengths); when the original position of clamps is reached, i.e., 4 cm distance, the shortened topsheet is held in this position for 60 seconds, before the second cycle starts, stretching the shortened topsheet up to 4.5Lt or 0.8Lt, optionally measuring the load forces applied at the various stages/lengths; when 4.5Lt or 0.8Lt, is reached again, the shortened topsheet is held in this position for 60 seconds, before the relaxation back to the original position, and the unload forces of this second unload cycle are measured for the various stages/lengths, as set out in the table above.

In this embodiment of the invention, the value of the first load and second unload forces are believed to be essential to the performance of the topsheet and representative for its elastic profile. Measurement of the first unload force and second load force may be performed, but is believed to be less representative for the force profile of the topsheet.

The topsheet preferably comprises elastic regions with elastic material which have an about similar elastic profile.

Preferred elastic materials used hereto include materials having a profile (measured in cross direction) like VFE-CD, available from Tredegar, and L-86, available from Fulflex (limerick, Ireland), or preferably L-89, available from Fulflex, or most preferred are of course one or more of these materials itself.

The materials typically have a thickness (e.g., gauge) of at least 20 microns, more preferably at least 40 microns, or even at least 60 microns, typically up to about 300 microns, or even up to 200 microns or even up to 150 microns. Highly preferred materials have a thickness of about 70 to 100 microns.

The length and width of the elastic regions on the topsheet will vary, typically depending on the exact dimensions of the topsheet and/or the article. An elastic region may be formed from a multitude of thin strands of the elastic material, or of a single band of elastic material.

For example, for size 4 diapers, the elastic region, in relaxed state, may be about 5 to 40 mm wide, preferably 8 to 30 mm, or even 10 to 25 mm.

In another embodiment of the invention, the article of the invention has a specific elastic profile, in order to provide the benefits of the invention, and thereto, it typically comprises one or more of the topsheets above and/or elasticated regions specified herein, having an about similar elastic profile.

The article has an elastic profile, based on a two-cycle hysteresis, measured by the method below, using a 500 mm/min clamp speed, which is as follows:

0.25L, by a first load force of less than 0.6 N, 0.55L, by a first load force of less than 5N or even less than 3.5 N and 0.8L, by a first load force of less than 10.0N or even less than 7.0N and a second unload force at 0.55$L_s$ of more than 0.4N, and a second unload force at 0.80$L_s$ of more than 1.4N or even more than 2.0N.

More preferably, the profile of the article is:
0.25$L_s$ by a first load force of less than 0.6 N, 0.40$L_s$ by a first load force of less than 1.5N, 0.60L, by a first load force of less than 2.8N, and 0.80$L_s$ by a first load force of less than 5.4N and a second unload force at 0.40$L_s$ of more than 0.1N, a second unload force at 0.60$L_s$ of more than 0.6N and a second unload force at 0.80$L_s$ of more than 2.0N.

Even more preferred is that the article has a profile of:
0.25$L_s$ by a first load force of less than 0.3N, 0.40$L_s$ by a first load force of less than 0.7N, 0.60$L_s$ by a first load force of less than 21.4N, and 0.80$L_s$ by a first load force of less than 53.2N and a second unload force at 0.40$L_s$ of more than 0.3N, a second unload force at 0.60$L_s$ of more than 0.7N and a second unload force at 0.80$L_s$ of more than 2.0N.

In addition, it may be preferred that the elastic profile of the article is as set out above, but then measured as a two-cycle hysteresis performed with a clamp speed of 10 mm/min.

Preferred profiles of the article of the invention are defined by the first load force and second load forces at all of the lengths in the following table (for a two cycle hysteresis with 500 mm/min clamp speed or even 10 mm/min):

|  | Preferred profile | More preferred profile | Even more preferred profile | Even more preferred profile | Most preferred profile |
|---|---|---|---|---|---|
| 1st Load at 0.25 $L_s$ |  | <0.6 N | <0.6 N | <0.5 N | <0.3 N |
| 1st Load at 0.30 $L_s$ |  | <0.9 N | <0.9 N | <0.8 N | <0.4 N |
| 1st Load at 0.35 $L_s$ |  | <1.2 N | <1.2 N | <1.1 N | <0.6 N |
| 1st Load at 0.40 $L_s$ | <2 N | <2.0 N | <1.5 N | <1.3 N | <0.7 N |
| 1st Load at 0.45 $L_s$ | <3 N | <2.5 N | <1.8 N | <1.6 N | <0.8 N |
| 1st Load at 0.50 $L_s$ | <4 N | <3.0 N | <2.1 N | <1.8 N | <1.0 N |
| 1st Load at 0.55 $L_s$ | <5 N | <3.5 N | <2.4 N | <2.1 N | <1.2 N |
| 1st Load at 0.60 $L_s$ | <6 N | <4.0 N | <2.8 N | <2.5 N | <1.4 N |
| 1st Load at 0.65 $L_s$ | <7 N | <4.5 N | <3.3 N | <2.9 N | <1.6 N |
| 1st Load at 0.70 $L_s$ | <8 N | <5.0 N | <3.9 N | <3.4 N | <2.0 N |
| 1st Load at 0.75 $L_s$ | <9 N | <6.0 N | <4.6 N | <4.1 N | <2.6 N |
| 1st Load at 0.80 $L_s$ | <10 N | <7.0 N | <5.4 N | <5.2 N | <3.2 N |
| 2nd Unload at 0.25 $L_s$ | — | — | — | — | — |
| 2nd Unload at 0.30 $L_s$ | — | — | — | >0.1 N | >0.1 N |
| 2nd Unload at 0.35 $L_s$ | — | — | — | >0.3 N | >0.2 N |
| 2nd Unload at 0.40 $L_s$ | — | — | >0.1 N | >0.5 N | >0.3 N |
| 2nd Unload at 0.45 $L_s$ | — | — | >0.2 N | >0.7 N | >0.4 N |
| 2nd Unload at 0.50 $L_s$ | >0.2 N | >0.2 N | >0.3 N | >0.9 N | >0.5 N |
| 2nd Unload at 0.55 $L_s$ | >0.4 N | >0.4 N | >0.4 N | >1.1 N | >0.6 N |
| 2nd Unload at 0.60 $L_s$ | >0.6 N | >0.6 N | >0.6 N | >1.3 N | >0.7 N |
| 2nd Unload at 0.65 $L_s$ | >0.8 N | >0.8 N | >0.8 N | >1.6 N | >0.8 N |
| 2nd Unload at 0.70 $L_s$ | >1.0 N | >1.0 N | >1.0 N | >2.0 N | >1.0 N |
| 2nd Unload at 0.75 $L_s$ | >1.2 N | >1.3 N | >1.3 N | >2.5 N | >1.3 N |
| 2nd Unload at 0.80 $L_s$ | >1.4 N | >2.0 N | >2.0 N | >4.0 N | >2.0 N |

The two-cycle hysteresis of an article herein is determined a two-cycle hysteresis measurement (following ASTM 76–96) performed as set out above for the topsheet two-cycle hysteresis measurement, which the change that the article is placed between to clamps in a horizontal tensile tester Z10/LH 1S, as available from Zwick (Ulm, Germany), whereby the clamps are positioned such that exactly the shortened article (portion) is between the clamps and such that exactly (and only) the shortened article length is not covered by the clamps. The clamps have at least the same size as the width of the article in the clamps, so that the clamps at least cover the total width of the article in the clamps. As above, the waiting period at maximum strain/stretch (0.8 $L_s$) as well as at the minimum strain/stretch (original position of clamp distance, i.e., 4 cm) is 60 seconds. During the measurement the equipment's software calculates all required parameters and determines thus the forces, strain/stretch, and total hysteresis curves).

The article preferably has a ratio of the load force to the unload force, determined as above with a two cycle hysteresis with 500 mm/min clamp speed which is:

($1^{st}$ Load 0.50 $L_s$/$2^{nd}$ Unload 0.50 Ls) is less than 20, preferably less than 7 or even less than 3; and ($1^{st}$ Load 0.65 $L_s$/$2^{nd}$ Unload 0.65$L_s$) is less than 9 or even less than 6, or even les and (1st Load 0.80 $L_s$/$2^{nd}$ Unload 0.80 $L_s$) of less than 7 or even less than 4 or even less th 1.5.

Preferred articles have each of the ratios in the vertical columns below:

|  | Preferred ratios | More preferred ratios | Even more preferred ratios | Even more preferred ratios | Most preferred ratios |
|---|---|---|---|---|---|
| 1st Load 0.25 $L_s$/ 2nd Unload 0.25 $L_s$ |  |  |  |  |  |
| 1st Load 0.30 $L_s$/ 2nd Unload 0.30 $L_s$ |  |  |  | <7 | <4 |
| 1st Load 0.35 $L_s$/ 2nd Unload 0.35 $L_s$ |  |  |  | <4 | <3 |
| 1st Load 0.40 $L_s$/ 2nd Unload 0.40 $L_s$ |  |  | <15 | <3 | <3 |
| 1st Load 0.45 $L_s$/ 2nd Unload 0.45 $L_s$ |  |  | <9 | <2 | <2 |
| 1st Load 050. $L_s$/ 2nd Unload 0.50 $L_s$ | <20 | <15 | <7 | <2 | <2 |
| 1st Load 0.55 $L_s$/ 2nd Unload 0.55 $L_s$ | <13 | <9 | <6 | <2 | <2 |
| 1st Load 0.60 $L_s$/ 2nd Unload 0.60 $L_s$ | <10 | <7 | <5 | <2 | <2 |
| 1st Load 0.65 $L_s$/ 2nd Unload 0.65 $L_s$ | <9 | <6 | <5 | <2 | <2 |
| 1st Load 0.70 $L_s$/ 2nd Unload 0.70 $L_s$ | <8 | <5 | <4 | <2 | <2 |

-continued

|  | Preferred ratios | More preferred ratios | Even more preferred ratios | Even more preferred ratios | Most preferred ratios |
|---|---|---|---|---|---|
| 1st Load 0.75 $L_s$/ 2nd Unload 0.75 $L_s$ | <8 | <5 | <4 | <2 | <2 |
| 1st Load 0.80 $L_s$/ 2nd Unload 0.80 $L_s$ | <7 | <4 | <3 | <1.5 | <2 |

In a preferred embodiment of the invention, the article herein has an opening, preferably an elongated split opening, leading to a void space, whereby the opening has longitudinal edges, along each one ore more elasticated regions are present, typically of the type described above. The elasticated regions maintain improved longitudinal and transverse alignment, as well as Z-direction proximity with a point of discharge on a wearer, e.g. stays in close proximity, preferably contact with the wearer.

Preferred is that the opening, positioned in at least the crotch region of the topsheet, is configured such that from 0%, or even from 10%, or even from 20% to 40% or even to 30% of the length of the opening extends from the transverse axis of the topsheet or article towards the front waist region, and the remaining percentage extends towards the back waistband.

The dimensions of the opening may vary, depending on the size of the topsheet and/or the article. Preferably, in particular for size 4 diapers, the length of the opening may be (e.g., in relaxed state) from 5 to 30 cm, or even from 10 to 25 cm, or even from 12 to 20 cm. The width of the opening of such articles (e.g., in relaxed state) is preferably from 2 to 10 cm and more preferably from 3 to 8 cm.

In a stretched state, the length of the opening may preferably be from 20 to 35 cm, and the width may preferably be from 3 to 6 cm.

The elasticated regions are preferably positioned along the two longitudinal edges of the opening (so that each edge has at least one elasticated region), extending from said opening towards the first (front) and second (back) waist region, preferably such that the end portions of the elastic regions can be attached or joined to the waist region. Thus, the elasticated regions are preferably longer than the opening, both in relaxed as in stretched state. Preferably, the elastic region is positioned over the full length of the active topsheet, e.g., the part of the topsheet which in use is intended to receive body exudates, typically the topsheet minus the parts thereof which form (part of) the waist region or band.

The length of the elastic region will typically depend on the size of the topsheet and/or the article. For example, for a size 4 diaper, the length of the elastic region in relaxed position may be 10 to 30 cm, or even 15 to 25 cm, and in stretched position preferably from 20 to 60 cm or even 25 to 45 cm or even 30 to 40 cm.

The elastic region may be in the form of two or more substantially parallel elasticated zones, and, preferably, the elasticated regions are shaped such that the middle portions of the regions are substantially parallel to one another, while the end portions (at least in relaxed state) bend away from one another (in the plane of the topsheet), so that the distance between the end portions of the elastic regions is larger that the distance between the middle portions of the elastic regions. Then, the end portions of the elasticated regions each typically make an angle with the longitudinal axis of the opening, preferably each angle being between 20° and 30°, and preferably such that the angle between the end portions of the elasticated regions is about twice as much, e.g., between 40° and 60°. This is herein referred to as an X-shape, and a preferred x-shape is exemplified in FIG. 1, as described herein after. In this preferred embodiment in contracted state, the preferred maximum distance between the elastic regions along each longitudinal edge of the opening is at least 150% of the minimum distance between the elastic regions.

Preferably, when in relaxed state, the elastic regions or part thereof are under an angle with the adjacent topsheet, such that the elastic regions are (also) bending out of plane of the topsheet, bending upwards and away from the void space (under the topsheet).

Due to the elastic profile of the article, the article is typically stored and packed in folded state, typically folded at least twice around transverse folding lines. For example, a preferred diaper herein may be folded twice, around two different transverse lines, to thus obtain a folded diaper of less than ½ of its original unfolded length, e.g., about ⅓ of the original length.

The invention is equally applicable to absorbent articles such as pull-on or training pants, pant-type diapers, incontinence briefs, incontinence undergarments, absorbent inserts, diaper holders and liners, feminine hygiene garments, bandages and the like; however, a preferred embodiment of an absorbent article of the present invention is a pull-on or training pants or diaper, preferably a unitary disposable absorbent article diaper, shown and described hereinafter. Thus, while the invention is described in detail with reference to a (baby, infant or adult) diaper, or pull-on/training pants, this description is equally applicable to other wearable article.

The topsheet, herein may be liquid pervious or impervious. It may be highly preferred that the topsheet is liquid pervious in one direction, but liquid impervious in the opposite direction, e.g., that body fluids may penetrate through the topsheet to the remaining part of the diaper, but that no or limited amounts of fluid can penetrate in reverse direction, towards the wearer's skin. For example, the topsheet may be treated with a chemical such that it is hydrophilic on one side and hydrophobic at the opposite side, as described hereinafter.

The topsheet is positioned adjacent the body facing surface of the backsheet or absorbent core, if present, and the longitudinal edges of the topsheet are preferably joined or attached to the longitudinal edges of the backsheet, by any attachment means known in the art, such as those described above. In one preferred embodiment of the present invention, the topsheet and the backsheet are attached directly to each other in some locations and are indirectly joined together in other locations by directly joining them to the leg cuffs of the diaper.

The topsheet defines an opening, typically an elongate slit opening, which provides a passage way to a void space, between the topsheet and the backsheet, or typically the topsheet and the core, when present.

The topsheet is fully or partially elasticated, such that the above defined force profiles and stretched and contracted shortened article lengths are achieved. Preferably, the topsheet comprises thereto elasticated regions, preferably at least along the longitudinal edges of the opening. Preferably, the elastic regions are one or more elastic bands or strands, positioned along the longitudinal edges of the opening, and preferably extending in both the front and back direction, towards or into the front and back waist regions. Preferably, the elastic regions are connected to the front and back waist region, or even fastened onto the front and back waist regions. The elasticated regions are preferably in the shape of an X, whereby the end portions of the elasticated regions bend away from one another, e.g., such that the distance between the end regions of the elasticated regions, both on the front and back side, is larger than the distance between the middle points of both elasticated regions.

The preferred width of the elasticated regions, and positions thereof are described hereinafter in more detail, both for articles of the invention in stretched state as for articles in contracted state.

Preferred articles herein have has a specific height $H_1$, which is at least 0.25 $L_s$, more preferably 0.3 $L_s$, or even 0.35 $L_s$ or even 0.4 $L_s$ or even 0.45 $L_s$, whereby $H_1$ can be follows.

The article's core has two longitudinal edges and a transverse axis, which intersects with the two longitudinal edges in two intersections. The core is fixed into a fixed, horizontal position by attaching the two intersection points to a horizontal flat surface, namely by two intersection areas each of about 0.5 cm extending in both longitudinal directions from the actual intersection point. Thus, the core is fixed in transverse direction and can thus not fold around a longitudinal axis, for example.

The topsheet with the opening with elastic regions then lies on top of the core, e.g., not facing the surface.

Then, the topsheet is pulled upwards, along a force line perpendicular to the core, e.g., vertically upwards, along the height $H_1$, with a force of 1 N or less, preferably even 0.2N or less. Hereby, the topsheet is pulled upwards by pulling the geometrical center point upwards; if the geometrical center point is located in the opening of the topsheet, then the topsheet is pulled upwards by the two point located on the topsheet, which are in transverse direction closest to the geometrical center point of the topsheet. The pulling can be done by any means, for example by attaching a small hook to the relevant point(s) of the topsheet and puling the hook upwards, while measuring the force applied, as to not exceed the above specified forces.

The $H_1$ is than the shortest distance between the geometrical center point of the core and the pulled up geometrical center point of the topsheet.

The above-mentioned forces are chosen such that the topsheet is only straightened or extended, without elastically deforming and elastically extending.

This measurement method to determine $H_2$ is particularly applicable when the article has longitudinal stiff core.

In another preferred embodiment of the invention, the article has a specific height $H_2$, which is at least 0.3 $L_s$, more preferably 0.35 $L_s$, or even 0.4 $L_s$ or even 0.45 $L_s$ or even 0.5 $L_s$, whereby $H_2$ can be determined as follows.

The core's geometrical center point is determined and an area of 1 cm² is marked around this center point. The core is fixed into a fixed, horizontal position by attaching this 1 cm² to a horizontal flat surface. Thus, the core is centrally fixed. The topsheet is on top of the core, e.g., not facing the surface.

The fixed core is then folded along its longitudinal axis, so that the core is generally folded upon it self (and the two halves are in contact with one another), and pressed with a force of 100N.

Then, the topsheet is pulled upwards, along a force line perpendicular to the core, e.g., vertically upwards, along the height $H_1$, with a force of 1 N or less, preferably even 0.2N or less. The application of this force and the puling upwards of the topsheet is done as above.

The $H_2$ is then the shortest distance between the geometrical center point of the core and the pulled-up geometrical center point of the topsheet.

The above-mentioned forces are chosen such that the topsheet is only straightened or extended, without elastically deforming and elastically extending.

This measurement method to determine $H_2$ is in particular applicable when the article has a core, which is longitudinally bendable, as is the case with the cores used in most diapers, when the legs of the user put pressure on the core and thereby bend the core. Then, this method resembles thus at best the real in-use situation.

In another preferred embodiment of the invention, the article has a specific height $H_3$, which is at least 0.3 $L_s$, more preferably 0.35 $L_s$, or even 0.4 $L_s$ or even 0.45 $L_s$ or even 0.5 $L_s$, whereby $H_3$ can be determined as follows.

The article submitted to this measurement has a backsheet and topsheet which are connected to one another along their longitudinal edges, i.e., at each side, at least the portion of the longitudinal edge of the backsheet at the intersection of the transverse axis of the backsheet and said edge is attached to at least the portion of the longitudinal edge of the topsheet at the intersection of the transverse axis of the topsheet and said edge, and typically the whole length of the edges are attached. Thus, two connection areas are formed which each have a inner connection line, which is the longitudinal edge line of the connecting area, closest to the geometrical center point A of the backsheet (which is also determined for this measurement, by the manner defined above), and an outer connection line, which is the opposite longitudinal edge line of the connecting area. The transverse axis through point A intersects each connection edge in point B. Each point B has a corresponding point C on the topsheet, which are the intersection points of the transverse axis of the topsheet and the outer connecting line. Also the geometrical center point D of the topsheet is determined. $H_3$ is then distance (A to B) plus the distance (C to D).

The connection referred to above may be a very thin connection area, formed when the topsheet and backsheet are placed next to one another and then connected, and then the inner connection line and outer connection line are about identical and point B and C are typically about the same point; or the connection area may be wider, formed by forming an area of overlap between the topsheet and the backsheet and then connecting the overlapping area. It may also be the case that the topsheet and backsheet are not directly connected to one another, but that one or more other components of the article indirectly connect(s) the topsheet and the backsheet. Then, the connecting area is typically the whole area between the longitudinal line or area where the backsheet is connected to this other component, up to the line where the topsheet is connected to this component, and the inner and outer connecting lines of the connecting area are then as defined above, i.e., the closest line to the geometrical center point of the backsheet A and the closest line to the geometrical center point of the topsheet D, respectively.

In a preferred embodiment herein the topsheet has longitudinal folds, and in that case, the distance from C to D is the absolute distance, i.e., the distance of the flattened out topsheet.

In a preferred embodiment, the article of the invention is an adult or infant diaper with a 'rise' $L_T$, which is the shortest distance $L_T$ from the belly button of the wearer to the small of the back of the wearer, measured via the crotch, which is in use larger than $L_c$, preferably such that $L_c$ is at least 20% less than $L_T$, more preferably at least 30% or even at least 40% or even at least 50% or even at least 60%. 'In use' means that this is the case when the diaper is first put on, as well as during use and when the diaper comprises bodily fluids, in particular fecal matter.

The topsheet is preferably compliant, soft feeling, and non-irritating to the wearer's skin.

A suitable topsheet may be manufactured from a wide range of materials, such as porous foams; reticulated foams; apertured plastic films; or woven or non-woven webs of natural fibers (e.g., wood or cotton fibers), synthetic fibers (e.g., polyester or polypropylene fibers), or a combination of natural and synthetic fibers. If the topsheet includes fibers, the fibers may be spun bond, carded, wet-laid, melt blown, hydro entangled, or otherwise processed as is known in the art. One suitable topsheet comprising a web of staple length polypropylene fibers is manufactured by Veratec, Inc., a Division of International Paper Company, of Walpole, Mass. under the designation P-8. Suitable formed film topsheets are described in U.S. Pat. No. 3,929,135, U.S. Pat. No. 4,324,246; U.S. Pat. No. 4,342,314; U.S. Pat. No. 4,463,045; U.S. Pat. Nos. 4,609,518 and U.S. Pat. No. 4,629,643. Such formed films are available from The Procter & Gamble Company of Cincinnati, Ohio as "DRI-WEAVE" and from Tredegar Corporation of Terre Haute, Ind. as "CLIFF-T."

Preferably, the topsheet is made of a hydrophobic material or is treated to be hydrophobic in order to isolate the wearer's skin from liquids contained in remaining part of the diaper. For example, if the topsheet is made of a hydrophobic material, preferably at least the upper surface of the topsheet is treated to be hydrophilic so that liquids will transfer through the topsheet more rapidly. This diminishes the likelihood that body exudates will flow off the topsheet rather than being drawn through the opening of the topsheet. The topsheet can be rendered hydrophilic by treating it with a surfactant or by incorporating a surfactant into the topsheet. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344; U.S. Pat. No. 4,988,345; U.S. Statutory Invention Registration No. H1670, published on Jul. 1, 1997 in the names of Aziz et al.

Any portion of the topsheet may be coated with a lotion as is known in the art. Examples of suitable lotions include those described in U.S. Pat. No. 5,607,760; U.S. Pat. No. 5,609,587; U.S. Pat. No. 5,635,191; U.S. Pat. No. 5,643,588; and WO 95/24173.

The diaper also comprises a typically liquid impervious backsheet. Preferably also an absorbent core is present, which is preferably positioned between at least a portion of the topsheet and the backsheet. There may be a secondary topsheet present, positioned between the core and the topsheet. The diaper may have side panels, and/or more preferably elasticized one or more leg cuffs. The diaper typically has a first or front waist region a second or back waist region, opposed to the first waist region, and a crotch region, located between the first waist region and the second waist region. The crotch region is typically that portion of the diaper which, when worn, is between the legs of the wearer. The waist regions of the diaper, when worn, typically gather or encircle the waist of the wearer and are generally at the highest at the highest elevation of the article, when the wearer is in the standing, upright position. The waist region, or preferably the waistband typically comprises the force line of the diaper.

Typically, the waist regions of the diaper have a portion, which is or forms the waistband. In one type of diapers, the waistband is open prior to use and needs fastening around the waist of the wearer. Thereto, the diaper preferably has a fastening system, typically joined to the waist region or band. Preferred fastening systems are described hereinafter in more detail, a most preferred system involving fastening tabs and landing zones, whereof the fastening are part of one waist region and the landing zones are part of the opposite waist region. Diapers herein which serve as pull-on or training pants have typically a waist region, which is a unity, and which is already fastened prior to use.

The backsheet is generally that portion of the diaper positioned adjacent the garment facing surface of the topsheet, or core, if present, which prevents the body fluids or exudates absorbed and contained therein from soiling articles which may contact the diaper, such as bedsheets and undergarments. In preferred embodiments, the backsheet is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials, which permit vapors to escape from the diaper while still preventing exudates from passing through the backsheet.

The backsheet, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. SELF webs suitable for the present invention are more completely described in U.S. Pat. No. 5,518,801.

The backsheet may be attached or joined to the topsheet, the absorbent core, or any other element of the diaper by any attachment means known in the art. It may be highly preferred that the edges of the topsheet and backsheet are directly attached to one another, but that the longitudinal edges of the topsheet and the core are not attached to one another, or optionally only partially attached.

The attachment means may include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

The absorbent core, which is preferably present, may comprise any absorbent material which is generally compressible, conformable, non-irritating to the wearer's skin, and capable of absorbing and retaining liquids such as urine and other certain body exudates, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; super absorbent polymers; absorbent gelling materials; or any other known absorbent material or combinations of materials. Exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147,345; U.S. Pat. No. 5,260,345; U.S. Pat. No. 5,387,207; and U.S. Pat. No. 5,625,222.

The diaper may also include a sub layer disposed between the topsheet and the backsheet. The sub layer may be any material or structure capable of accepting, storing or immobilizing bodily exudates. Thus, the sub layer may include a single material or a number of materials operatively associated with each other. Further, the sub layer may be integral with another element of the diaper or may be one or more separate elements joined directly or indirectly with one or more elements of the diaper. Suitable materials for use as the sub layer may include large cell open foams, macro-porous compression resistant non woven highlofts, large size particulate forms of open and closed cell foams (macro and/or microporous), highloft non-wovens, polyolefin, polystyrene, polyurethane foams or particles, structures comprising a multiplicity of vertically oriented looped strands of fibers, absorbent core structures described above having punched holes or depressions, and the like. (As used herein, the term "microporous" refers to materials that are capable of transporting fluids by capillary action. The term "macroporous" refers to materials having pores too large to effect capillary transport of fluid, generally having pores greater than about 0.5 mm in diameter and more specifically, having pores greater than about 1.0 mm in diameter.)

The diaper may comprise at least one elastic waist feature that helps to provide improved fit and containment. The elastic waist feature is generally positioned in the waistband. It is generally intended to elastically expand and contract to dynamically fit the wearer's waist. The elastic waist feature may be constructed in a number of different configurations including those described in U.S. Pat. No. 4,515,595 and U.S. Pat. No. 5,151,092.

The diaper preferably comprises a fastening system. The fastening system preferably maintains the first waist region and the second waist region in a touching or overlapping configuration so as to provide lateral tensions or force line about the circumference of the diaper to hold the diaper on the wearer. The fastening system preferably comprises tape tabs and/or hook and loop fastening tabs, although any other known fastening means are generally acceptable. Some exemplary fastening systems are disclosed in U.S. Pat. No. 3,848,594; U.S. Pat. No. 4,662,875; U.S. Pat. No. 4,846,815; U.S. Pat. No. 4,894,060; U.S. Pat. No. 4,946,527; U.S. Pat. No. 5,151,092; and U.S. Pat. No. 5,221,274; and U.S. Pat. No. 4,963,140.

In alternative embodiments, the article is to be used as a pull-on type diaper, such as a training pant. Then, typically, the opposing sides of the garment may be seamed or welded to form a pant, such that the front waist portion or waistband and a back waist portion or waist band are (irremovably) connected prior to use, by a first connection area and a second connection area. The force line is then defined by these connecting areas.

The diaper preferably further includes leg cuffs that provide improved containment of liquids and other body exudates. Leg cuffs may also be referred to as leg bands, side flaps, barrier cuffs, or elastic cuffs, as described in; U.S. Pat. No. 3,860,003; U.S. Pat. No. 4,808,178 and U.S. Pat. No. 4,909,803; U.S. Pat. Nos. 4,695,278 and 4,795,454.

Preferred may be that the diaper includes a topical lotion for the skin of the wearer, and or a topical adhesive or body adhering composition which acts to hold the opening further in place during use. Typically, this is comprised by the topsheet or part thereof, so as to further improve the alignment of the opening in the topsheet with for example the anus of the wearer. The topical adhesive may be located on the topsheet, or the body adhering composition may (also) be integral with the material making up the topsheet or other element of the absorbent article or may be a separate material disposed directly or indirectly on all or any portion of the absorbent article. Further, the body adhering composition may be disposed on any portion of the absorbent article in any pattern or configuration including, but not limited to lines, stripes, dots, and the like. In one preferred embodiment, the topical adhesive is present on the elasticated regions along the edges of the opening. Suitable body adhesives are known in the art.

Preferably, the diaper includes a thermally activatable adhesive, which acts to hold the article or some portion thereof in place during use. A "thermally activatable" adhesive is an adhesive that exhibits an increase in "tack" or adhesion after being warmed to a temperature at or above the activation temperature of the adhesive. The "activation temperature" of a thermally activatable adhesive is the temperature at which the adhesive is activated (i.e., the temperature at which the adhesion of the adhesive increases significantly, as described herein). In certain embodiments wherein the maximum adhesion is achieved over a range of temperatures, the activation temperature is the temperature at which the increase in adhesion begins. Preferably, the activation temperature of the thermally activatable adhesive is between about 28° C. and 60° C. or even about 30° C. and 40° C. However, the activation temperature may be any temperature that may be reasonably experienced in the context of an absorbent article. However, in cases where the activatable adhesive is used, for example, only during application of the article and not expected to be active during the article's use, the adhesive preferably remains active between about 33° C. and about 60° C., more preferably between about 37° C. and about 49° C. and even more preferably between about 39° C. and about 45° C.

The activatable adhesive may also be thermally deactivatable and/or thermally reversible. A thermally deactivatable adhesive exhibits a decrease in "tack" or adhesion after being cooled to a temperature at or below the deactivation temperature of the adhesive. The "deactivation temperature" of a thermally deactivatable adhesive is the temperature at which the adhesive is deactivated (i.e., the temperature at which the adhesion of the adhesive decreases significantly, as described herein). A thermally reversible adhesive may be activated by an increase in temperature and, subsequently, deactivated by a corresponding decrease in temperature. The "deactivation temperature" of a thermally reversible adhesive is the temperature at which the adhesive is deactivated (i.e., the temperature at which the adhesion of the adhesive decreases significantly, as described herein). The activation temperature and deactivation temperature of thermally reversible adhesives may be the same or different temperatures.

The activation temperature of thermally activated topical adhesives activated by skin temperature will typically be between about 33° C. and 38° C., more preferably between about 35° C. and 37° C.

The thermally activatable adhesive of the present invention may be a crystallizable polymer or a functional equivalent of a crystallizable polymer having a weight average molecular weight in the range of about 20,000 to 2,300,000 Daltons, typically 100,000 to 1,300,000 Daltons, and more typically 250,000 to 1,000,000 Daltons. Further, the polymer chains in the crystallizable polymer composition may optionally be cross-linked to provide greater physical stability of the adhesive. The adhesive composition may optionally include additives as known in the art, such as filers, tackifiers, antioxidants, and the like. The adhesives of the present invention may be applied to or coated onto any substrate by any means known in the art. Suitable substrates are preferably breathable films as described herein for use as backsheets, polyolefinic films, non-wovens, highlofts, formed films, apertured films, and the like. One exemplary thermally activatable adhesive is described as Example 1 in U.S. Pat. No. 5,387,450. Other examples of thermally activated adhesives suitable for use in the claimed invention are described in more detail in U.S. Patent Nos. 5,156,911 and 5,648,167. An exemplary thermally reversible adhesive is described as Example 2 in the above-referenced U.S. Pat. No. 5,387,450.

Preferred Processes to Make the Article of the Invention

Preferred articles of the invention herein are obtained by a process wherein one or more elastic bands or strands is/are applied along the longitudinal axis of a topsheet, e.g., a nonwoven material, such that one or more elastic region(s) is/are obtained which extends along about the whole length L of the article, or even along the whole length of the active topsheet, i.e., that part of the topsheet which in use acts to receive body exudates, positioned between the forcelines of the article, around the waist of the wearer, e.g., the length of the topsheet minus the parts which form (part of), or are attached to the waist regions or waistbands. While the elastic material may be applied such that the elastic regions are in the form of two separate substantially parallel elastic zones, or for example in an Y-shaped form or V-shaped form, it is preferred that the elastic material is applied such that an X-shaped elasticated region is obtained, as described above. Preferred dimensions of the elastic region are described herein.

The non-woven may already contain an opening along its longitudinal axis, so that then the elastic bands or strands are typically attached to either longitudinal edge of the opening, such that the end portions of the elastic bands or strands bend away from the opposing end portions of the opposing elastic bands or strands, such as to form an X-shaped elastic region. Alternatively, the non-woven may not yet contain an opening, and then, the elastic bands or strands are in a X-shape, prior to attachment to the non woven, whereafter a slit opening is cut through both a part of the non-woven and a part of the elastic band/strands (together referred to as laminate), along the longitudinal axis of the non-woven and the band or strands.

Any method may be used to attach the elasticated region to the topsheet, including the methods described above for attaching the backsheet to other parts of the article, and including heatbonding and gluing methods Preferred glues include H2031, available from ATO-Findley and/or HL-1620 available from H.B. Fuller (St Paul, USA).

In a non-limiting example, two elastic band of L-89 elastic material, available from Fulflex, with (in relaxed state) a thickness of about 70 microns, a width of 20 mm and a length of 16 cm, are obtained and also a sheet of a polypropylene non-woven, available as P-14 from Veratec, Inc. of Walpole, Mass., which is 25 cm wide and 50 cm long (i.e., in the direction of stretch) in a relaxed state.

In relaxed state, a slit opening with a length of 20 cm and a width of 4 is cut in the non-woven.

One elastic band is glued in a stretched state to each longitudinal edge of the opening of the non-woven. This is done such that the middle 11 cm (16 cm minus areas of 2.5 cm at both ends, which are used later for attachment) of the elastic film is stretched to about the length of the non-woven, minus the length of the front and back areas reserved to form the front and back waistband (2×2.5 cm) and minus the length needed to attach the elastic film on both sides (2×2.5 cm) (e.g., 50 cm−(2×2.5 cm)−(2×2.5 cm)=40 cm).

Each elastic band is glued on the non-woven in a manner that the ends of the bands bend away from the ends of the opposing elastic band, in the shape of an X. Preferably, this is done such that, in after application, the distance between to the ends of the (end portions or regions of the) strands is 80 mm in contracted state, while the distance between the center point of the strands is only 40 mm, in contracted state.

The angles between the end portions of the strands are as mentioned above, e.g., preferably 40–60°.

Thus, a stretched, elasticated topsheet with a slit opening having two elasticated bands along the edges, in the shape of an X is obtained, whereby each end of the elastic film is located 25 mm from the edge of the non-woven (i.e., the edge intended to be in the front or back waist region of a finished diaper).

The total length of the topsheet is preferably less than 300 mm, or even less than 260 mm or even les than 240 mm, and the shortened topsheet portion length is preferably less than 160, or even less than 120 mm or even less than 100 mm.

The topsheet may be used on a Pampers Premium Size 4 diaper, designed for a baby weight range of 21–37 pounds, or may replace the topsheet of such a diaper. Thereto, the topsheet with the elastic bands are attached to the front and back waistbands.

Alternatively, an elastic strand in the shape of an X can be applied to a non-woven topsheet, which does not yet comprise a slit opening, in the manner above. Then, after application of the X-shaped elastic band, a slit opening is cut in the elastic/non-woven laminate, in a manner specified above. Thus, a topsheet similar to the topsheet above is obtained, which can then be incorporated in a size 4 diaper, as above.

The dimensions and other parameters of the exemplary diaper embodiments described above can be readily modified by one skilled in the art to smaller or larger wearers, including adult wearers.

Preferred Articles of the Figures

Preferred articles of the invention are now being described with reference the FIGS. 1, 2 and 3.

FIG. 1 is a plan view of the diaper 20 in its stretched state, with portions of the structure being cut away to more clearly show the underlying structure of the diaper 20 and with the portion of the diaper 20 which contacts the wearer facing the viewer. One end portion of the diaper 20 is configured as a first waist region 36 of the diaper 20. The opposite end portion is configured as a second waist region 38 of the diaper 20. An intermediate portion of the diaper 20 is configured as a crotch region 37 that extends longitudinally between the first and second waist regions 36 and 38. The waist regions 36 and 38 generally comprise those waist portions of the diaper 20 which, when worn, encircle the waist of the wearer. The waist regions 36 and 38 includes elements which can gather about the waist of the wearer to provide improved fit and containment, or which typically can gather around the waist and can be fastened around the waist by use of fastening means, such as tabs 27, which are fastened to landing zones 29.

The crotch region 37 is that portion of the diaper 20 which, when the diaper 20 is worn, is generally positioned between the legs of the wearer.

The shortened article portion 70 is the portion of the diaper 20 between the transverse lines 71 and 72, line 71 being the line through the lowest point of the fastening tabs 27 and line 72 being the transverse line through the lowest point of the landing zones. The stretched shortened article length $L_s$ in FIG. 1 is thus the shortest distance, i.e. parallel to the longitudinal axis x, between the lines 71 and 72.

The diaper 20 comprises a topsheet 24, a liquid impervious backsheet 26, and an absorbent core 28 encased between the topsheet 24 and the backsheet 26. The topsheet may include regions of reduced permeability to fecal material.

The topsheet 24 comprises a slit opening 30, along the longitudinal axis x of the diaper 20, which is configured to receive fecal exudates and isolate at least a portion of the exudates from the skin of the wearer.

The topsheet 24 may be fully or partially elasticated. In FIG. 1, the topsheet 24 is partially elasticated by the provision of elastic bands 31 and 32, which have an X-shape.

The slit opening 30 is located in the topsheet 24 such that the fecal exudates pass through the opening into a void space formed between the topsheet 24 and the absorbent core 28 and/or other underlying layers such as sub layers, acquisition layers and the like. The void space entraps or encapsulates bodily waste. It is also contemplated that the void space may be formed between two elements of the diaper 20, including but not limited to the topsheet 24 and the backsheet 26, the acquisition layer and the core 28, the core 28 and the backsheet 26, etc. Alternatively, the void space may be formed between a secondary topsheet and a primary topsheet, which are disposed in a face-to-face arrangement and joined along the edges such that the secondary topsheet faces the skin of the wearer and the primary topsheet faces the underlying layers. For this embodiment, the void space is in communication with a slit opening in the secondary topsheet.

The slit opening 30 in the topsheet 24 is located in alignment with the wearer's anus during use. Preferably, the slit opening 30 in the topsheet 24 is located in a target zone of the diaper. The target zone is that portion of the diaper, which is configured to directly receive the insult of fecal matter from the wearer and is generally located in the crotch portion of the diaper. Particularly, in one non-limiting embodiment, the target zone may extend from about 5 to about 30 centimeters in length along the longitudinal axis x of the diaper with about one fourth of its length extending longitudinally from the lateral axis y of the diaper 20 towards the first or front waist region 36 and the remainder extending longitudinally towards the second or back waist region 38, when measurements are made with the topsheet in a fully extended or stretched state. Generally, about 0% to about 40%, preferably 10% to 35% or even 20% to 30% of the slit opening 30 may be located forward of the lateral centerline on the diaper 20.

The slit opening 30 in the topsheet 24 is generally disposed in the target zone along the longitudinal axis x and is defined by two opposing longitudinally extending side edges 40, a front edge 41 and a back edge 42. The front edge 41 is generally located in the crotch region 37 of the diaper 20 towards the first, front region 36, or in the first waist region 36 itself, while the back edge 42 is located in the crotch region 37 near the second waist region 38, or in the second waist region 38 itself. The slit opening 30 includes a length in the longitudinal direction parallel to the longitudinal axis x of the diaper and a width in the lateral direction which is parallel to the lateral axis y of the diaper 20. The length of the slit opening 30 is within the ranges specified above.

The diaper 20 preferably also includes a fastening system, typically including at least one engaging component (or fastener of male fastening component) 27 and at least one landing zone 29 (female fastening component), such as hook-loop type fastening systems. The diaper 20 may also include such other features as are known in the art, including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092 which are incorporated by reference herein.

The diaper 20 of the present invention includes an elastically foreshortened topsheet including elasticated regions 31 and 32, along at least portions of the longitudinal edges 40 of the slit opening 30. The elastic regions 31 and 32 ensure that the opening 30 of the diaper 20 is positioned and remains positioned in the gluteal groove of the buttocks, including the perianal region.

The edge 40 of the slit opening may be held against the wearer's skin allowing the feces to penetrate the slit opening 30 without deflection, via only the elastic forces supplied by the elastic regions 31 and 32, or optionally additionally by use of a body adhering composition, as described above. In any case, it is preferred that the body adhering composition permit vapors to pass (i.e., breathable), be compatible with the skin and otherwise skin friendly. Further, it is preferred that the body adhesive be at least partially hydrophobic, preferably 60%, more preferably 80%, by weight of the adhesive consist of hydrophobic components. However, hydrophilic adhesives are contemplated in certain embodiments of the present invention.

The elasticated regions 31, 32 may be formed by bonding pre-stretched elastic bands along the longitudinal edges 40 of the slit opening 30, by the method described herein.

The width of the elasticated regions 31, 32 in stretched state, measured laterally from the longitudinal edges 40 of the slit opening 30 is within the ranges specified above. The width of the slit opening in stretched state 30 is preferably also as specified above.

The elastic regions 31, 32 extend from the slit opening 30 in the direction of the waist regions, preferably in a X-shape, with front elastic regions 43 and 44 and/or back elasticated regions 45 and 46. In stretched state, preferred maximum distance between the elastic regions 32 and 31 is at least 150% of the minimum distance between the elastic regions 31, 32.

Figure 2:
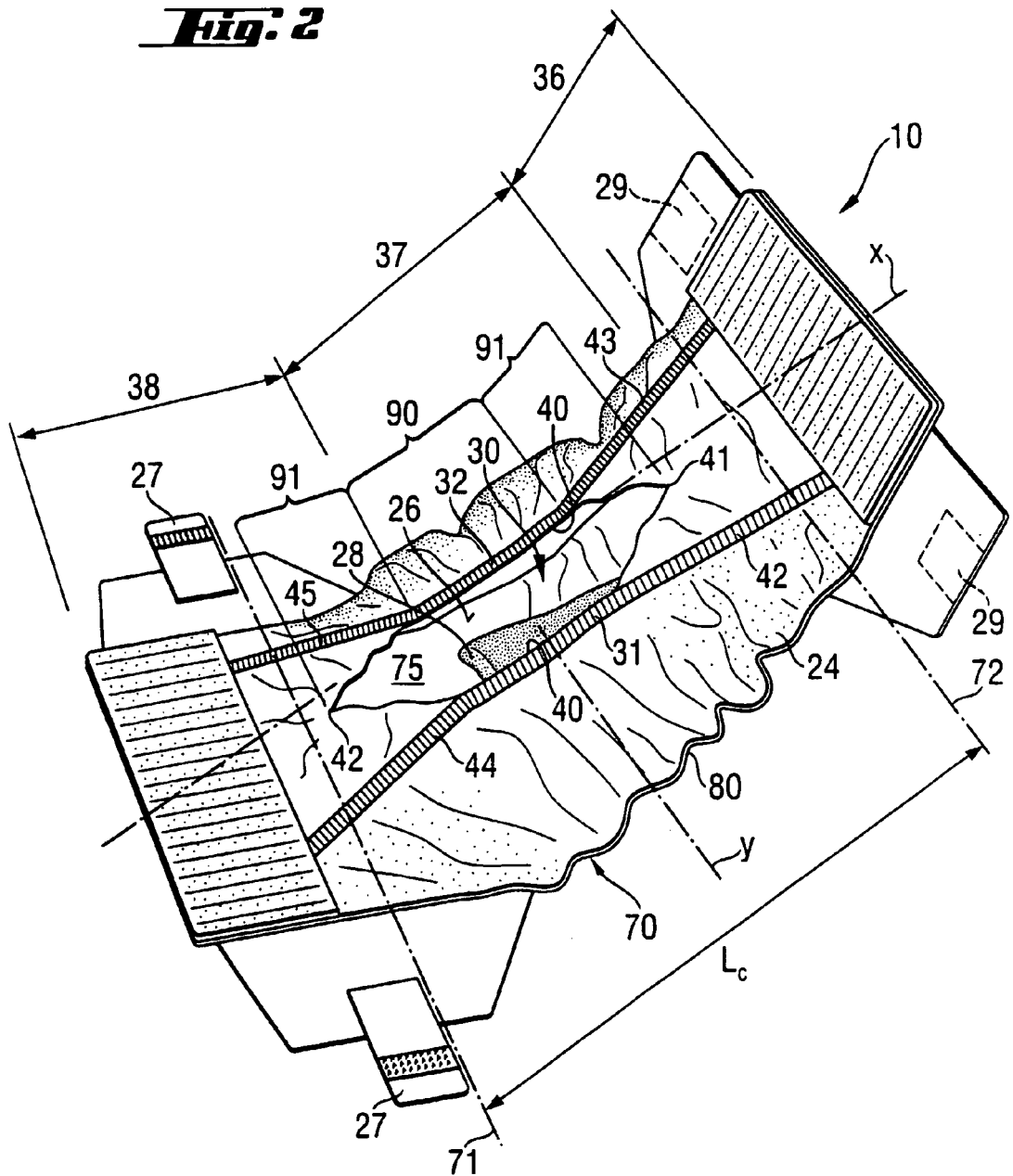
FIG. 2 is perspective view of a preferred disposable diaper of the present invention.

FIG. 2 shows how the diaper 20 in contracted state. The elastic regions 31, 32 are in the shape of an X, and extend along the slit opening 30 into the waist regions 36, 38, and are attached to the waistbands. The elastic regions 31, 32 have an angle with the joining topsheet 24, such that the elastic regions bend away from the void space and the backsheet 26 and core 28.

The contracted shortened article length $L_c$ is the shortest distance, i.e., parallel to the longitudinal axis x, between the transverse lines 71, 72, which are transverse to the lowest point of the fastening tabs 27 and landing zones 29, respectively.

The width, length of the elasticated regions 31, 32 and opening 30, in contracted state, is as specified above.

The elastic regions 31, 32 preferably extend from the slit opening 30, as can be seen in FIG. 1, in the direction of the waist regions, preferably in a X-shape, with front elastic regions (or portions) 43 and 44 and/or back elastic regions (or portions) 45 and 46.

In contracted state, the preferred maximum distance between the elastic regions 32 and 31 is at least 150% of the minimum distance between the elastic regions 31, 32.

The slit opening 30 leads to a void space 75, for receiving bodily fluids.

Unlike the slit opening 30 in FIG. 1, it may be more preferred that the article has a slit opening which has a hexagonal shape. An example of such a hexagonal shaped slit opening 30 is shown in FIG. 2. The slit opening 30 contains a rectangular portion 90 and two triangular portions 91 at each side thereof. The length of the slit opening 30 is then measured from the joining point of the edges of the opening 30, in the top of the triangulars 91 (i.e., the length of the longest dimension/longitudinal axis of the hexagonal slit opening 30) and has the preferred values are as specified herein. The width of the hexagonal slit opening 30 is then the width of the transverse axis of this slit 30, orthogonal to the longitudinal axis of the slit opening 30.

The longitudinal edges of the crotch region of topsheet 24 of diaper 20 of FIGS. 1 and 2 are not attached to the core 28 of the diaper 20. They are typically attached or joined to the backsheet 26 of the diaper 20 and optionally to the leg cuffs, if present. Preferred may even be that the complete longitudinal edges of the topsheet 24 are not attached to the core 28.

The topsheet 24 comprises folds which unfold when a low force, such as less than 1N is applied to the geometrical center point of the topsheet 24, typically by applying 1 N force on the middle point of an elasticated edge 32. The topsheet 24 can thus be extended in use. This ensures that when the backsheet 26 and core 28 become heavier due to the received bodily fluids, and start sagging downwards, the topsheet 24 can merely extend and remain in position, in close proximity to the wearer's skin.

Also, the limited attachment or no attachment of the topsheet 24 to the core 28 ensures that, when the diaper 20 receives bodily exudates and the core 28 and backsheet 26 are pulled downwards, due to the weight of the exudates received by the diaper 20, the topsheet 24 and the slit opening 30 do not move automatically with the core, but remain against the skin of the wearer, or in very close proximity to the wearer.

The diaper 20 also has leg cuffs 80 on both longitudinal edges of the diaper 20, typically attached to the backsheet 26. Preferred is that the longitudinal edge of a leg cuff 80, the longitudinal edge of the topsheet 24 and the longitudinal edge of the backsheet 26 are attached together in the form of a thin, longitudinal attachment edge.

Figure 3:
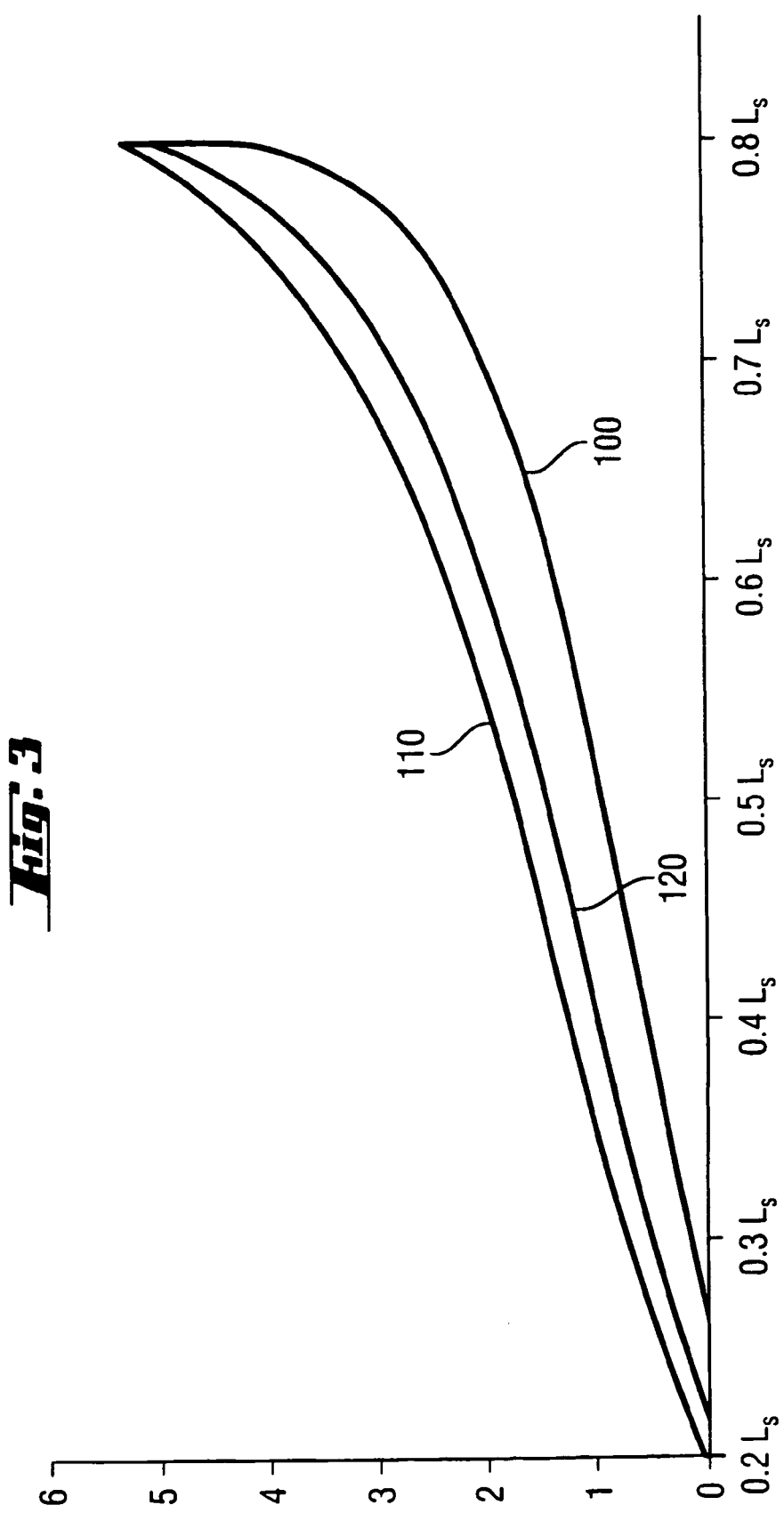
FIG. 3 is a force-strain curve related to measurements performed on a disposable diaper of the invention, like the diaper shown in FIGS. 1 and 2.

FIG. 3 is a graph which shows the two-cycle hysteresis elastic force profile curves for a preferred diaper of the invention, such as made by the process examples herein, and for example, shown in FIG. 2, having elastic bands of TK12.5.

It shows, along the y-axis, the force applied to the diaper using the method described herein to determine the two-cycle hysteresis, stretching the diaper to a length, which equals $0.8L_s$, thereby passing through various lengths which are fractions of $L_s$, indicated along the x-axis.

The 1st unload curve and the 2nd unload curve of this execution are about similar, and the curves almost fall on top of one another and they are thus shown in the graph as one unload curve 100 (namely the lowest curve 100 in the graph).

The highest curve is the 1st Load curve 110. The middle curve is the 2nd Load curve 120.

The about vertical line at the point on the x-axis corresponding to 0.8 Ls represents the force loss during the 60 seconds waiting period between the application of the load force and before commencing of unload force, at this length 0.8 Ls.

The diaper subject of the measurement of which the results are shown in this graph has a force profile which ensures that the topsheet remains in contact with the skin of the user, even when the diaper is heavily soiled and larger forces pull the diaper backsheet and core down, because the unload and load curves are very close, whilst not requiring too high a load force to achieve this, and thus being more comfortable in use.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a topsheet and a backsheet joined together and forming a first waist region, a second waist region, a crotch region interposed between the waist regions, and a void space between the topsheet and the backsheet for receiving bodily exudates, the absorbent article having a longitudinal axis and a lateral axis,
    wherein the topsheet has a slit opening providing access into the void space, the slit opening being positioned in at least the crotch region, extending along the longitudinal axis, and having longitudinally extending laterally opposing side edges, the topsheet also having longitudinally extending laterally opposing elasticated regions disposed along the respective side edges of the slit opening, the elasticated regions being laterally spaced apart a least distance in the crotch region and diverging laterally toward each of the waist regions, thereby forming an X-shape,
    the slit opening having an irregular hexagonal shape including longitudinally opposing triangular portions, where the side edges of the slit opening converge together to form longitudinally opposing first and second end edges of the slit opening having the forms of points where the side edges meet, and a rectangular portion connecting the triangular portions, the side edges being substantially parallel to each other in the rectangular portion.

2. The absorbent article of claim 1 further comprising a first elastic waistband disposed in the first waist region and a second elastic waistband disposed in the second waist region, the elasticated regions extending longitudinally from the first elastic waistband to the second elastic waistband.

3. The absorbent article of claim 2 wherein the elasticated regions comprise elastic bands extending longitudinally between and being attached to the first elastic waistband and the second elastic waistband.

4. The absorbent article of claim 1 wherein the absorbent article is a disposable diaper and further comprises an absorbent core encased between the topsheet and the backsheet.

5. The absorbent article of claim 4 wherein the void space is formed between the topsheet and the absorbent core.

6. The absorbent article of claim 1 wherein the first end edge is disposed distant from the lateral axis in a direction toward the first waist region and the second end edge is disposed distant from the lateral axis in a direction toward the second waist region.

* * * * *

UNITED STATES PATENT AND TRADEMARK OFFICE
CERTIFICATE OF CORRECTION

PATENT NO. : 7,223,261 B2
APPLICATION NO. : 10/764850
DATED : May 29, 2007
INVENTOR(S) : Joerg Mueller et al.

It is certified that error appears in the above-identified patent and that said Letters Patent is hereby corrected as shown below:

Title Page
After the Related U.S. Application Data, insert:
-- (30)    Foreign Application Priority Data
   July 26, 2001   (EP)……………..01117670 --.

INID Code (57)    Abstract
Line 12 of the abstract text, delete "contacted" and insert -- contracted --.

Column 2
Line 2, delete "on" and insert -- of --.
Line 4, delete "remain" and insert -- retains --.
Line 6, delete "waist" and insert -- weight --.
Line 10, delete "to" and insert -- the --.

Column 3
Line 52, delete "plan" and insert -- plane --.
Line 60, delete "of" and insert -- to --.

Column 4
Line 16, delete "sate" and insert -- state --.

Column 5
Line 53, delete "to" and insert -- two --.

Column 8
Line 4, delete "limerick" and insert -- Limerick --.
Line 35, delete "0.25L," and insert -- $0.25L_s$ --.
Line 35, delete "0.55L," and insert -- $0.55L_s$ --.
Line 37, delete "0.8L," and insert -- $0.8L_s$ --.
Line 43, delete "0.60L," and insert -- $0.60L_s$ --.

Column 10
Line 38, delete "les" and insert -- less than 2; --.
Line 40, delete "th" and insert -- than --.

Column 11
Line 16, delete "ore" and insert -- or --.

UNITED STATES PATENT AND TRADEMARK OFFICE
CERTIFICATE OF CORRECTION

PATENT NO. : 7,223,261 B2
APPLICATION NO. : 10/764850
DATED : May 29, 2007
INVENTOR(S) : Joerg Mueller et al.

It is certified that error appears in the above-identified patent and that said Letters Patent is hereby corrected as shown below:

Column 12
Line 17, delete "x-shape" and insert -- X-shape --.

Column 13
Line 29, insert -- determined as -- before the word "follows".

Column 15
Line 9, delete "$L_T$" and insert -- $L_r$ --.
Line 10, delete "$L_T$" and insert -- $L_r$ --.
Line 13, delete "$L_T$" and insert -- $L_r$ --.

Signed and Sealed this

Sixth Day of May, 2008

JON W. DUDAS
*Director of the United States Patent and Trademark Office*